United States Patent [19]

Ranney et al.

[11] 4,423,153

[45] Dec. 27, 1983

[54] METHODS AND COMPOSITIONS FOR THE DETECTION AND DETERMINATION OF CELLULAR DNA

[75] Inventors: David F. Ranney, Dallas, Tex.; Alfred J. Quattrone, Westlake, Calif.

[73] Assignee: Board of Regents, The University of Texas System, Austin, Tex.

[21] Appl. No.: 327,104

[22] Filed: Dec. 3, 1981

[51] Int. Cl.$^3$ ............................................ G01N 33/52
[52] U.S. Cl. ......................................... 436/63; 435/6; 436/174
[58] Field of Search .......................... 23/230 B; 435/6; 436/63, 174

[56] References Cited

U.S. PATENT DOCUMENTS 4,302,437 11/1981 Herbert .............................. 435/6 X
4,345,027 8/1982 Dolbeare ........................... 436/63 X

OTHER PUBLICATIONS

B. T. Hill, Anal. Biochem., 70(2), 635–638 (1976).
Chemical Abstracts, 88:185709w (1978).

Primary Examiner—Sidney Marantz
Attorney, Agent, or Firm—Arnold, White & Durkee

[57] ABSTRACT

Fluorochrome compositions and methods for the selective detection and determination of double stranded, helical DNA are provided. DNA is quantitated by determining the fluorescence enhancement imparted from the formation of a highly specific DNA-fluorochrome adduct. The fluorochrome composition disclosed includes a divalent metallic cation and a fluorescent antibiotic, antineoplastic agent selected from mithramycin, chromomycin or olivomycin. A compatible surfactant can also be included with the fluorochrome composition to enhance solubilization of cellular matter. Moreover, a compatible membrane penetrating agent such as dimethyl sulfoxide can be included with the composition to accelerate solubilization of the cellular matter. The compositions and methods provided are also useful for the screening or quantitating of agents which interact with DNA to induce displacement of fluorochrome bound to DNA.

42 Claims, 2 Drawing Figures

METHODS AND COMPOSITIONS FOR THE DETECTION AND DETERMINATION OF CELLULAR DNA

BACKGROUND OF THE INVENTION

The present invention relates to bioanalytical methods and compositions; and more particularly it relates to improved fluorometric assay methods and fluorochrome compositions for selectively evaluating DNA content of cells or for screening for compounds that interact with crude, partially purified and purified DNA.

Various pathological conditions and chemotherapeutic regimens suppress lymphocyte activation. For example, patients with cancer, immunodeficiency diseases, organ grafts, autoimmune disease, and acute drug toxicity may exhibit an inhibition of lymphocyte activation. As a consequence of suppressed lymphocyte activation, these patients also incur increased susceptibility to serious infection, even susceptibility to ordinarily innocuous fungi, bacteria and viruses. The chronic effects of suppressed lymphocyte activation are correlated with a higher incidence of developing various cancers, particularly lymphomas and sarcomas. Furthermore, in patients with existing specific types of cancer, autoimmune disorders and infections, the intercurrent impairments of lymphocyte responsiveness correlate respectively with enhanced rate of tumor growth, exacerbation of autoimmune pathology and accelerated infection. In some cases, these invader-host imbalances are produced by soluble mediators synthesized and released into patient sera by the tumors, autoimmune tissues and infectious agents themselves.

One reliable, in vitro, measure of lymphocyte activation is the degree of DNA synthesis that occurs within the cell population following stimulation with an appropriately presented antigen, mitogen (lectin), host mediator, pharmaceutical or environmental agent. Deoxyribonucleic acid (DNA) is a complex and intricate nucleoprotein which through messenger RNA, provides the genetic coding for enzymes, antibodies and other cell proteins. Suppressed lymphocytes, both T and B cells, almost always exhibit a corresponding suppression of spontaneous and/or stimulated DNA synthesis.

At present, the principal in vitro test for assessment of lymphocyte activation involves a microtiter culture procedure using tritiated thymidine, a radiolabelled precurser of DNA or other cellular components, which become incorporated into lymphocyte DNA and other cellular metabolites, affording an approximate measure of the rate of DNA synthesis. Several problems, however exist with implementation of this technique as a diagnostic bioanalytical assay. A primary drawback of the conventional $^3$H-thymidine assay is the susceptibility of cellular uptake, metabolism, and eventual incorporation of the $^3$H-thymidine into DNA to interference by multiple normal and abnormal serum components, test substances and byproducts which have either no effects or no directly proportional effects on DNA synthesis. Often false results are obtained because soluble test substances released by necrotic tumor cells from cancer patients, macrophages from autoimmune patients and experimental animals, abnormal lymphoid tissues from immunodeficient patients, and mass production commercial systems for natural products such as hybridoma cultures and bacterial fermentation vats include interfering substances such as "cold nucleosides" which compete for the $^3$H-thymidine uptake into cellular components. Hence, the nonspecificity of $^3$H-thymidine as an indicator of DNA synthetic rates results in false, high or low, indications of lymphocyte activation.

Furthermore, the $^3$H-thymidine assay test suffers from the disadvantages inherently connected with radioisotopic materials and techniques, such as their incumbent expense, health hazards, waste disposal problems and laboratory licensing requirements.

Accordingly, there remains a need for a more specific assay for lymphocyte activation, and modulators thereof, than the $^3$H-thymidine assay. It would be advantageous to provide such methods that eliminate both artifactual suppression and enhancement of lymphocyte activation which are commonly produced by thymidine, adenosine, deoxyadenosine and other cold nucleosides, ribavirin, vincristine, vinblastine, colchicine and other natural and synthetic products.

In addition to overcoming or circumventing the many drawbacks associated with prior art lymphocyte activation assays, the present invention also offers a selective screening system for substances that may interact with DNA.

Many compounds which directly interact with, bind to or alter the conformation of DNA also exhibit mutagenic, carcinogenic and/or immunotoxicant activities. Furthermore, many antineoplastic agents modulate cell replication by binding to DNA thereby altering its primary structure, destabilizing the double helix and/or depolymerizing the polynucleotide sequence.

Recently, fluorescence polarization techniques and instruments have been developed to compare the DNA binding characteristics of chemotherapeutic agents (such as actinomycin) and carcinogenic agents by competitive binding against the fluorescent, intercalating probe, acridine orange. While fluorescence polarization represents an elegant approach to the screening of DNA-interactive compounds that constitute potentional carcinogens and antitumor agents, instrument expense and difficulties achieving the modes of automation required to process large sample numbers have precluded its widespread industrial, commercial, and clinical application. Moreover, many of the fluorochrome systems employed are not specific for DNA, but rather exhibit binding activity with other related nucleotides including synthetic monostranded nucleoprotein, noneucaryotic nucleotides and RNA.

Accordingly, it would be advantageous to provide a rapid, automated inexpensive procedure that is based on fluorescence enhancement rather than polarization, and that can utilize standard fluorometers as well as polarization type fluorometers for the detection and quantitative determination of compounds which bind selectively to DNA. Further, it would be advantageous that such procedures utilize composition and mixtures having long shelf lives which concomitantly afford the sensitivity required for routine lymphocyte activation assays employed by clinical, commercial and basic research laboratories.

SUMMARY OF THE INVENTION

Double stranded, helical DNA is a product of both eucaryotic and procaryotic organisms. Synthesis of DNA at the cellular level serves as the basis for the genetic coding necessary for cell replication and differentiation. In addition, for many specialized cells, such as the lymphocytes, DNA is believed to be the memory bank and code for the induction and synthesis of antibodies, the body's immunologic defense mechanism against infection and antigen invasion.

In many disease states, such as cancers, immunodeficiencies, transplantations, drug toxicity, and autoimmune diseases there is an interference with either the spontaneous or induced synthesis or activity of DNA. In some instances either the disease state itself or altered soluble products associated with the disease state will inhibit the synthesis of DNA within the cells without necessarily killing the respective cells. Although the cells may continue to survive for a time, they will be unable to replicate, undergo clonal expansion, sustain tissue integrity or subserve body defense functions. In other instances the DNA synthesis may go unchecked, but a substance associated with the disease state may bind to or interact with the DNA in such a way as to alter DNA conformation thereby rendering the DNA inactive or deviant. Moreover, exogenous toxins may interact with a cell-surface or cytoplasmic receptor other than DNA thereby indirectly suppressing DNA synthesis or activity.

The present invention offers a simple, rapid and inexpensive method, which is readily adapted to automation, for the detection and determination of intracellular, double stranded, helical DNA in either the presence or absence of cellular debris.

In accordance with this invention an aqueous composition is provided comprising a divalent metallic cation cofactor in the form of a salt; a fluorochrome, such as mithramycin, which in the presence of the cofactor is capable of fluorescence enhancement upon interaction with double stranded, helical DNA; and a small concentration of a compatible surfactant which is effective to enhance the solubility of DNA and cellular debris in aqueous solution. Further, a small concentration of a low molecular weight, water soluble, organic solvent may be included in the composition, the solvent serving as a membrane or cell wall penetrating agent facilitating the influx or surfactant and fluorochrome into the cell and enhancing solubilization of cellular constituents.

In a first implementation of the methods of this invention, the fluorochrome composition thus provided, in contact with DNA, is capable of imparting fluorescence enhancement upon the formation of a DNA-fluorochrome complex, the fluorescence enhancement being in direct proportion to the concentration of native helical DNA present within a cell sample.

In a second application of the methods of this invention, test agents are screened for the extent of competitive binding to DNA relative to a reagent fluorochrome. Fluorescence enhancement is first measured for a mixture of a known amount of reagent fluorochrome and a subsaturating amount of DNA. By the addition of increasing concentrations of an appropriate, DNA-interactive test agent, displacement of the fluorochrome results. The negative change in fluorescent enhancement value corresponds directly to the extent of DNA binding or modification by the test agent.

If the test compound itself is fluorescent, the greatest sensitivity and specificity of this screening assay requires that at least one of the following conditions be met: (1) either the excitation or emission maxima specific for the reagent fluorochrome should be separated by at least 20 nm from those of the test compound and (2) at the concentration where the test compound inhibits 50% of the fluorescence increment due to the reagent florochrome: DNA binding, the fluorescence contribution of the mixture of test compound plus DNA without fluorochrome should be a small-to-moderate fraction (i.e. <20%) of the total fluorescence increment.

DETAILED DESCRIPTION OF THE PREFERRED EMBODIMENT

Figure 1:
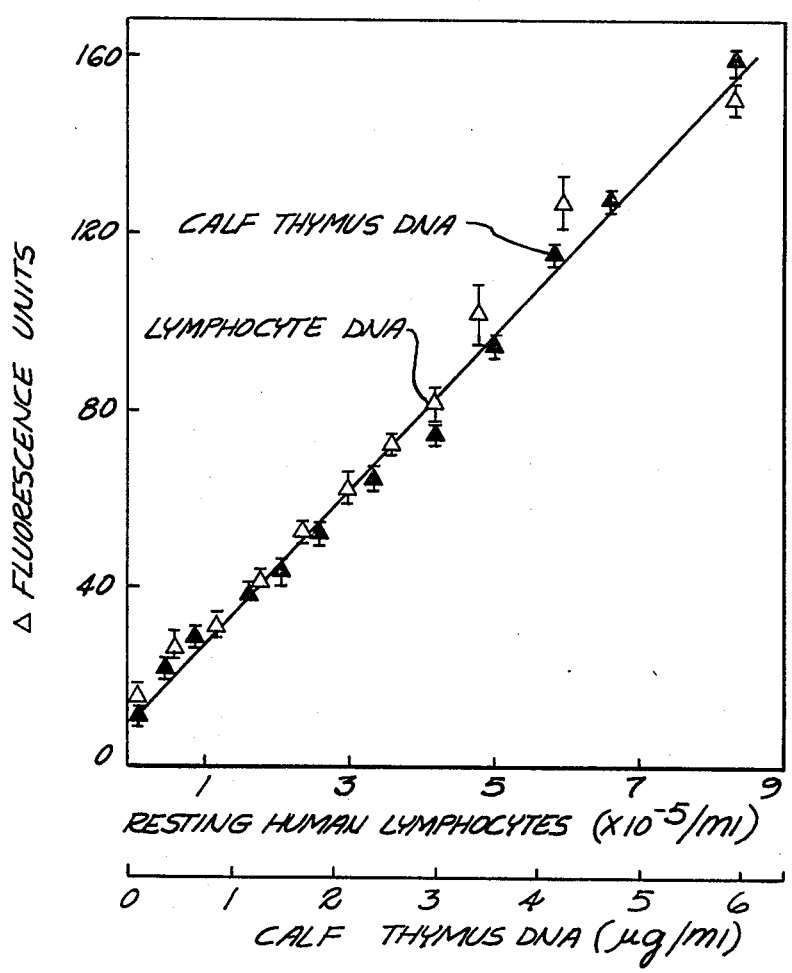
FIG. 1 shows the relative fluorescence intensity enhancement curves for mithramycin bound in the presence of $Mg^{+2}$ to solubilized human peripheral blood lymphocyte DNA (Δ) and to calf thymus DNA (▲); Δ fluorescence units were measured as [(mithramycin bound DNA)-(reagent blank containing mithramycin)].

This invention will be described in terms of preferred embodiments which represent the best mode known to applicants at the time of this application.

In accordance with a first embodiment of the present invention there is provided a fluid composition comprising a fluorochrome, a divalent metallic cation in the form of a salt, and a compatible surfactant. This composition provides an indicator media useful for the selective detection and determination of native double stranded, helical DNA and for the determination of compounds that inhibit DNA-fluorochrome binding.

Fluorescence enhancement is the increased fluorescence intensity exhibited by a fluorochrome upon interaction with a substrate as compared to the intrinsic fluorescence of the fluorochrome. Such a differential in fluorescence can be correlated to the extent of binding of the fluorochrome to the substrate and ultimately is an indication of the amount of available substrate present within a sample. Fluorescence enhancement is an analytical technique often used to detect and quantitate substrate concentration.

The fluorochrome provided in the context of the present invention is a fluorescent compound selected from a class of antibiotic substances which exhibit a selective binding capacity with double stranded, helical DNA and which are capable of fluorescence enhancement upon interaction with DNA. In particular, the fluorochrome of the present invention is desirably an antineoplastic, antibiotic containing the chromomycinone complex. Such fluorochromes include aureolic acid, chromomycin, and olivomycin. Specifically, mithramycin, chromomycin $A_3$ and olivomycin are representative fluorochrome compounds from each respective class listed above. The preferred fluorochrome of the present invention is mithramycin, antibiotic LA-7017, an antibiotic isolated from Streptomyces.

Mithramycin is particularly useful in this composition because it exhibits a high degree of fluorescence enhancement upon interaction with DNA thereby culminating in a highly sensitive detector assay suitable for microtiter cell samples. In addition, mithramycin is specific for double stranded, helical DNA, thereby obviating the contribution of nonspecific fluorescent enhancement upon binding with RNA, other polynucleotides and nucleoproteins, proteins and other cytoplasmic and cytoskeletal constituents, present in cell samples.

It has been observed by Applicants and others that the binding of fluorochromes to substrates often requires stabilizers or as sometimes termed "cofactors", to produce a stable fluorescent complex. Accordingly, Applicants have demonstrated that a divalent metallic cation is required as a cofactor to stabilize the DNA-fluorochrome complex and impart the enhanced fluorescence. Suitably, the cofactors of the present invention include $Mg^{+2}$, $Zn^{+2}$, $Mn^{+2}$, and $Co^{+2}$, with $Mg^{+2}$ being particularly preferred. The cofactor is typically provided in the form of a salt, suitably a halide salt, although salts of weak inorganic or organic acids may be employed.

It is believed that the function of the divalent cation cofactor is to counterbalance the electrorepulsive force imparted by the anionic nature of the antibiotic, antineoplastic fluorochrome relative to the negatively charged phosphate groups exposed on the DNA substrate.

Also included in the composition is a compatible surfactant. A surfactant is useful in the present methods for the selective determination of DNA in the presence of cellular matter. The surfactant serves to solubilize or emulsify cellular matter thereby promoting contact between the intracellular DNA and fluorochrome, the latter being a large enough molecule that it encounters transport difficulty across intact cellular and intracellular membranes. Further, the surfactant facilitates dispersion of the cellular matter in an aqueous solution such that reproducible sample fluorescence readings can be obtained without further separation of the DNA-fluorochrome complex from cellular debris.

In the context of this invention, a compatible surfactant is a dispersing agent which does not fluoresce significantly under the conditions and at the wavelengths used to measure the fluorescence of the DNA-fluorochrome complex, nor does the surfactant quench such fluorescence, nor does it promote dissociation of the DNA-fluorochrome complex at the concentrations of the surfactant employed. Suitable compatible surfactants preferably include the water soluble higher alkyl sulfonates, such as sodium dodecyl sulfonate. Other suitable surfactants useful in the present invention include the polyoxyethylene ethers, e.g. 23-lauryl ether (Brij 35 marketed by Sigma Chemical Co., St. Louis, Mo.) and Zwitterionic detergents such as sulfobetaine.

Further, the compositions of this invention may include a compatible, low molecular weight, water soluble, organic solvent that serves as a cell membrane and/or cell-wall penetrating agent. The penetrating agent accelerates and enhances the entry of both surfactant and fluorochrome into the cells. The resulting is to both accelerate and increase the solubilization of intracellular DNA, cell membranes and other cytoskeletal structures, and thereby to improve the interaction between fluorochrome and DNA such that the assay may be performed more rapidly with greater specific fluorescence intensity (signal-to-noise ratio) and greater precision than is possible in the absence of penetrating agent.

In the context of this invention, a compatible penetrating agent is small, water soluble organic solvent or cell fixative that penetrates membranes and/or cell walls rapidly and acts as a carrier vehicle, cell membrane denaturant and/or dehydrating agent to facilitate the transmembrane transport of the fluorochrome and ionic surfactant, but which does not fluoresce significantly under the conditions and at the wavelengths used to measure fluorescence of the DNA-fluorochrome adduct, nor does it quench such fluorescence, nor does it promote dissociation of the DNA-fluorochrome complex at the concentrations of agent employed. The preferred compatible agent is the water soluble organic solvent, dimethyl sulfoxide (DMSO). Other suitable agents useful in the present invention include the low molecular weight, water soluble organic solvents, methanol, ethanol and glycerol, and the low molecular weight, organic membrane fixatives such as formaldehyde, glutaraldehyde, and 2,3-butanedione.

In accordance with the methods of detection and determination of double stranded, helical DNA of the present invention, the compositions described above are adapted for use in the presence of cellular debris, thereby obviating the need to isolate the DNA from cellular debris prior to fluorescence measurements. Accordingly, cell samples with the imputed DNA are first solubilized by disruption so as to render the cellular debris in the form of ultrafine particles. Disruption of cells is typically achieved through physical means such as centrifugation, sonification, or freeze-thawing. Sonification is a preferred technique since this results in an ultrafine homogeneous dispersement of cellular matter, and hence leads to optimal precision and reproducibility of fluorescence readings.

Prior to, concomitant with or subsequent to the cell disruption, a surfactant or dispersing agent is added to effect solubilization of the cellular matter. "Solubilization" as used herein connotes the various forms in which substances can be dispersed in a fluid medium, including suspensions, solutions, emulsions and dispersions.

After the DNA and cellular debris are suitably solubilized and sufficient time is allowed for optimum fluorochrome DNA binding, fluorescent measurements are taken directly using a suitable fluorometer. No further separation procedures such as separating any excess unbound fluorochrome form the fluorochrome-DNA complex is required.

In order that the methods of the invention may be more clearly understood, the preferred embodiments will be further described in terms of the following examples, which should not be construed to limit the scope of this invention.

EXAMPLE I

Determination of DNA Content of Lymphocyte Cultures in the Implementation of a Lymphocyte Activation Assay This assay system was performed by selectively stimulating either T lymphocytes [with concanavalin A, 0.1 to 20 ug/ml, or phytohemagglutinin, 0.1 to 4.0% (v/v)] or B lymphocytes [with pokeweed mitogen, 0.5 to 25% (v/v)]. The mitogens were added to human peripheral blood lymphocytes, or to single cell suspensions of animal lymphoid organs, in standard, round-bottom, 96-well microtiter culture plates (linbro #76-012-05, Linbro Scientific, Inc., Hamden, Conn.). The cells plus mitogens in replicates of four were incubated in 200 $\mu l$ of RPMI 1640 culture medium containing 8% serum (AB for human cultures; fetal calf for animal cultures) at 37° C. in a humidified environment of 5% $CO_2$ for the usual 3-to-5 day culture intervals classically employed for mitogen stimulated $^3H$-thymidine assays. At the end of the incubation interval, the cell supernatants were suctioned away from the centrifuged cell pellets and discarded. A 180 µL volume of detergent solution (comprising glass-filtered, aqueous, 0.01% (w/v) sodium dodecyl sulfonate (SDS), 5 mM $MgCl_2$ and 5 mM Trizma base (buffered to pH 7.4 with concentrated HCL) was added to the cell pellet in each mirotiter well, using a Micromedic Automatic Pipette (Micromedic Systems, Inc., Rohm and Haas, Philadelphia, Pa.) or other available automated pipetter. The trays were incubated for 1 hour to allow partial disruption of the cells and concomitant solubilization of intracellular DNA. Cellular disruption was completed by sonicating the microtiter trays from the bottom side up, using a modified inverted cuphorn-extension bath sonicator (Heat Systems, Model W370, Heat Systems Ultrasonics, Inc., Plainview, N.Y.).

Following sonic disruption of the cells, a 150 uL aliquot of each microtiter sample was withdrawn from the well, diluted with 600 uL of the fluorescent reagent and simultaneously transferred, using a Micromedic Pipette, into either an automated fluorometer cassette or manual fluorometer vial for fluorescence reading.

The fluorescent reagent was a filtered aqueous solution comprising 40 ug/ml (w/v) mithracin (manufactured by Pfizer Laboratories, N.Y., N.Y., containing 2.5% (w/w) mithramycin in mannitol and sodium dihydrogen phosphate, marketed by the Dome Division of Miles Laboratories, Inc., West Haven, Conn.), 12 mM $MgCl_2$, and 0.01% (w/v) SDS. Following its specific interaction with DNA, mithramycin undergoes fluorescence enhancement at λ ex/em 440/540 nm.

In the present assay system, Applicants have shown that this enhancement is related linearly to the quantity of double-stranded DNA present in the cell pellet solubilized from each microtiter well. Applicants also have shown that the magnitude of increases in DNA content per well, as measured by the present method, are related directly to the extent of DNA synthesis by the mitogen-activated lymphoid subpopulation. In addition, applicants have shown that the results of this present assay system correlate directly with those of standard (uncomplicated) $^3$H-thymidine assays, and classical diphenylamine assays for changes in DNA content.

Fluorescence enhancement was measured using several manual and automated fluorometers with interference grating excitation/emission monochromers and narrow band pass optical interference filters. Specific fluorometers used for the development, evaluation and automation of the present assay system include a Perkin-Elmer Model MPF-2A equipped with an Hitachi Model 018-0550 high sensitivity mirrored cuvette holder (manual mode); a Gilson Spectra Glo Filter Fluorometer equipped with 5-60X and 520-3M narrow band excitation and emmission filters, respectively, (manual and flow cell modes); and a Bio-Rad Fluoromatic photoncounting fluorometer (automatic, cassette wheel-flow cell mode), in which the standard fluorescein filters were replaced with two 430 nm narrow band (10 nm) excitation filters and with two emission filters consisting of a 520 nm narrow band (10 nm) element plus a 515 nm blocking element.

To perform sample readings, the diluted microtiter samples were introduced either into Kimble #60930-L 9×30 mm ¼-dram glass vials for manual loading into the Perkin Elmer or Gilson fluorometers, or into Falcon #2052 plastic tubes (Becton Dickinson & Co.) for loading into the cassette wheel of the Bio-Rad fluorometer for automated flow-cell photon counting (6 seconds per sample), and on-board data reduction. With the former two fluorometers, the output detectors measured integrated fluorescent light rather than individual photons, the outputs were plotted using a Linear Instruments strip chart recorder, and the data were reduced by the systems operator.

Fluorescence enhancement was calculated as Δ fluorescence units=[(mithramycin with disrupted cells)-(reagent blank containing mithramycin composition)]. The differences in Δ fluorescence enhancement then were compared for mitogen-stimulated versus unstimulated cultures.

A representative linear plot obtained for mithramycin fluorescence enhancement versus the concentration of solubilized lymphocytes is illustrated in FIG. 1. In the absence of mithramycin the solubilized cellular matter in FIG. 1 exhibits neglible fluorescence over the range of 0 to $9 \times 10^5$ cells.

EXAMPLE II

This assay system was performed in a fashion identical to that of Example I, above, except that at the end of the culture interval, at a point just after suction-removal of the cell supernatants, the solubilizing solution added to the cell pellets in the microtiter wells (at 180 uL/well) was modified in such a fashion that it contained, in addition to the exact ingredients (at the exact concentrations) described in Example I, the new ingredient, 10% (v/v) dimethyl sulfoxide (DMSO), as a membrane penetrating agent. The trays were incubated for one-half hour, in contrast to the 1-hour interval employed in Example I. The remainder of the assay was carried out with procedures and reagents identical to those of Example I. Applicants have shown that the new ingredient, as added in the present example, is effective to accelerate the solubilization of DNA from test cells and thereby to shorten the interval of incubation required prior to cell sonication. Furthermore, Applicants have shown that the addition of this new reagent to the solubilizing solution increases the average fluorescence intensity by 26% (at the midpoint of the working range of the assay) and produces a significant decrease in the coefficients of replicate variation.

EXAMPLE III

A series of samples containing known amounts of calf thymus Type I DNA (Sigma Chemical Co., St. Louis, Mo.) ranging from 0 to 6 µg/ml were analyzed according to the mithramycin assay. In Falcon #2052 plastic tubes, 150 µL of various concentrations of calf thymus DNA were added to 600 µL each of mithramycin fluorescent reagent to produce graduated standards. The mithramycin reagent comprised filtered, aqueous solution of 4 mg% (w/v) Mithracin (Pfizer Laboratories, Groton, Conn., containing 2.5% (w/w) mithramycin in mannitol and sodium dihydrogen phosphate), 0.01% (w/v) SDS, and 12 mM $MgCl_2$.

The contents of each standard curve tube were individually transferred into a standard fluorometer cuvette, and fluorescence measurements were performed at λ ex/em=440/540 nm, as described in Example I, using a Perkin Elmer MPF-2A spectrofluorometer equipped with an Hitachi Model 018-0050 high sensitivity mirrored cuvette holder and operated at the highest gain setting (No. 6).

Fluorescence enhancement in this example was measured as Δ Fluorescence units=[(mithramycin bound DNA)−(reagent blank containing mithramycin)]. Results are shown in FIG. 1. The fluorescence enhancement (Δ fluorescence units) for a sample containing an unknown amount of DNA can be determined similarly and the fluorescence enhancement used to determine the concentration of sample DNA from the standard curve generated from known concentrations.

EXAMPLE IV

Assay for Inhibition of DNA-Mithramycin Binding by the Test Agent, Ethidium Bromide—A Liquid Phase Fluorescence Detection System Ethidium Bromide is known to interact with DNA. Interaction of increasing concentrations of ethidium bromide with DNA results in progressive displacement of DNA-bound mithramycin and produces a corresponding decrease in fluorescent enhancement elicited from such a complex.

The inhibition of mithramycin-DNA binding by ethidium bromide was quantitated as follows. Calf thymus Type I DNA was solubilized at 10 mg/ml in aqueous reagent buffer containing 5 mM Tris-HCl (pH 7.35) and 5 mM $MgCl_2$. This DNA stock was diluted with reagent buffer to make a 5 μg/ml working solution. Crystalline mithramycin without additives (obtained from Pfizer Laboratories, Grodon, Conn.) was dissolved at 22 μg/ml in reagent buffer. Test samples of ethidium bromide (purchased from Sigma Chemical Co., St. Louis, Mo.) were dissolved and serially diluted in reagent buffer, 100 μL aliquots were placed into Falcon #2052 plastic assay tubes (amounts ranging from 0.03 to 5 μM). To each assay tube 1800 μL of DNA working solution was added and the mixture was incubated for 30 minutes at 22° C. One hundred microliters of mithramycin solution was added to the assay tubes, producing a final mithramycin concentration of 1.1 μg/ml.

The DNA-mithramycin test mixture was incubated for an additional 45 minutes at 22° C. to optimize the binding of mithramycin to DNA.

The assay tubes were loaded into the Bio-Rad Fluoromatic cassette wheel sampler and analyzed using the automated, photon-counting fluorometer (Bio Rad Fluoromatic, Bio Rad Laboratories, Richmond, Calif.). The standard fluorescein filters were replaced with excitation filters and emission filters optimized for mithramycin-DNA, as described in Example I. The microprocessor was set at a counting time of 6 seconds per sample.

The experimental increment (●) of fluorescence enhancement in the presence of test agent was calculated as:

photons (DNA+test agent+mithramycin)−photons (test agent+buffer)−photons (mithramycin+buffer)

Figure 2:
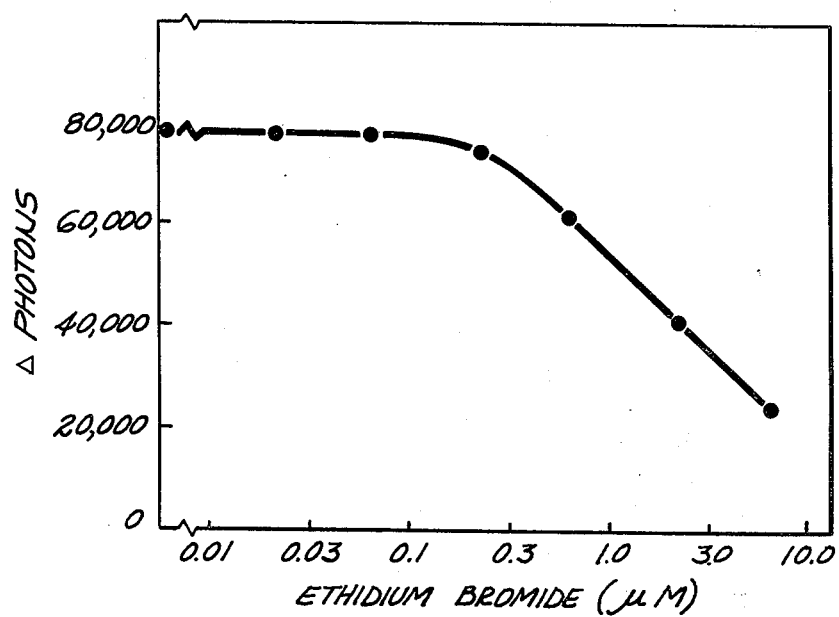
FIG. 2 shows a dose-response curve for inhibition by ethidium bromide of fluorescence enhancement resulting from mithramycin binding to solubilized, purified calf thymus Type I DNA (●). Also shown is the contribution to the total fluorescence enhancement made by ethidium bromide plus DNA in the absence of mithramycin (O).

The data are expressed in FIG. 2 as Δ photons vs. ethidium bromide concentration, plotted on a linear vertical scale and log horizontal scale. The control increment (O) of fluorescence enhancement produced by interaction of ethidium bromide with DNA (in the absence of mithramycin) was calculated as:

photons (DNA+test agent)−photons (test agent+buffer).

The contribution of this control fluorescence enhancement to the total fluorescence enhancement is neglible even at the highest concentration of ethidium bromide tested.

In the present assay system, Applicants have shown that a classical hyperbolic asymptotic saturation curve is obtained of fluorescence intensity versus increasing concentration of native double-stranded helical DNA, for a fixed (1.1 ug/ml) concentration of mithramycin added per assay tube. In addition, Applicants have shown that the lower portion of this curve (below 50% saturation of mithramycin by DNA, ie., below 50 ug/ml of DNA) is essentially linear, thereby allowing the measurement of directly proportional relationships between fluorescence intensities and the number of exposed functional binding sites on a fixed quantity of DNA (whose concentration is below the 50% saturation level, chosen in the present example to be 5 ug/ml).

EXAMPLE V

Assay for Inhibition of DNA-Mithramycin Binding by the Test Agent, Ethidium Bromide—Solid-Phase Fluorescence Detection System The inhibition of mithramycin-DNA binding by ethidium bromide was quantitated by an alternative method to that described in Example IV, above, in which the inhibition of fluorochrome-DNA binding was performed using a solid-phase system rather than a liquid-phase system. Calf thymus Type I DNA was solubilized at 10 mg/ml in aqueous reagent buffer containing 5 mM Tris-HCl (pH 7.35) and 5 mM $MgCl_2$. This DNA stock was diluted with reagent buffer to make a 500 ug/ml working solution. Crystalline mithramycin (without additives) (obtained from Pfizer Laboratories, Groton, Conn.) was dissolved at 110 ug/ml in reagent buffer. Test samples of ethidium bromide (purchased from Sigma Chemical Co., St. Louis, Mo.) were dissolved and serially diluted in reagent buffer and then diluted again (at 1:2 each) in the mithramycin solution, to produce a final mithramycin concentration in each tube of 55 ug/ml. A 20-uL aliquot of the DNA working solution was placed on the circular 7 mm (in diameter) cellulose nitrate filter of a two-sided research test stick (supplied by International Diagnostic Technology, Santa Clara, Calif.), to give a final quantity of 10 ug of DNA per filter, and the DNA was dried by gentle air blowing at 22° C. The filter on the opposite side of each stick was left untreated, and was used as a surface for control groups comprising ethidium bromide and mithramycin in the absence of DNA. As derivatized by the Applicants, these DNA reagent sticks had a shelf life of longer than one month. A 20-uL aliquot of each dilution of test agent in mithramycin was placed on both the experimental (DNA) side and control (blank) side of a test stick, producing a final quantity of 1.1 ug of mithramycin per filter (a quantity identical to that present in 1 ml of final reading solution in Example IV, above). The test sticks were air dried for 70 minutes at 22° C. to afford optimal mithramycin-DNA binding and maximal inhibition of binding by ethidium bromide. Both the experimental and control sides of each stick were evaluated for fluorescence intensity by inserting them serially into the reading window of a FIAX Model 100 Fluorometer (International Diagnostic Technology, Santa Clara, Calif.), which was equipped with standard fluorescein filters. The instrument gain was calibrated using low and high standards consisting of test sticks to which had been applied, respectively, mithramycin alone and mithramycin plus DNA. The increments of fluorescence enhancement in the presence of ethidium bromide dilutions were calculated as: relative fluorescence units (DNA+test agent+mithramycin)−relative fluorescence units (test agent+mithramycin). The data were plotted as the differences in relative fluorescence units (y-axis) versus concentration equivalents of ethidium bromide (x-axis), in a fashion analogous to that shown in FIG. 2. Concentration equivalents were defined as the molar ratios of ethidium bromide-to-mithramycin which were equal to those obtained in the liquid-phase assay of Example IV. The resulting $ID_{50}$ equivalent for ethidium bromide in the solid-phase assay was identical to that obtained in the liquid-phase assay (Example IV, FIG. 2).

In the present assay system, Applicants have shown that the same hyperbolic asymptotic DNA saturation curves (with linear lower segments) are obtained as those described in Example IV. Furthermore, Applicants have shown that, for all test agents compared, similar $ID_{50}$ concentrations for inhibition of mithramycin-DNA binding were given by the solid-phase and liquid-phase systems. Hence, both detection systems may be used for the screening and quantification of DNA-binding agents.

The foregoing description of the invention has been directed to particular embodiments for purposes of explanation and illustration. It will be apparent, however, to those skilled in this art that many modifications and changes in the composition and method of using the same can be made in the implementation and utilization of the present invention without departing from its concept of using the provided fluorochrome composition to assess the fluorescence enhancement relating to either the concentration of double stranded, helical DNA present in cellular matter or the extent of competitive or noncompetitive inhibition of mithramycin bending to crude or purified DNA by a test agent. For example it is contemplated that the methods of this invention can be adapted as a tool for the assessment of cellular and cell-mediated responses in the fields of immunology, oncology, transplantation surgery, fermentation and hybridoma cultures, pathology and toxicology. Furthermore, the methods of the invention are especially suitable for the rapid screening of immunomodulating agents including immunosuppressents, immunoenhancers, natural mediators and carcinogens and mutagens which interfere either directly or indirectly with DNA synthesis or activity. These and other applications of the illustrated embodiments, as well as other embodiments of the invention, will be apparent to those skilled in this art without departing from the scope of the invention as described in the following claims.

What is claimed is:

1. A fluid composition, adapted for use in selectively detecting and determining the cellular content of double stranded, helical DNA in the presence of cellular debris, comprising in aqueous solution:
   a divalent metallic cation cofactor;
   a fluorochrome which in the presence of the cofactor is capable of significant fluorescence enhancement upon interaction with double-stranded, helical DNA;
   a small concentration of a compatible surfactant which is effective to enhance solubilization of DNA and cellular debris.

2. The fluid composition in accordance with claim 1 wherein said divalent metallic cation is selected from the group consisting of $Mg^{+2}$, $Mn^{+2}$, $Zn^{+2}$ and $Co^{+2}$.

3. The fluid composition in accordance with claim 1 wherein the divalent metallic cation is $Mg^{+2}$.

4. The fluid composition in accordance with claim 1 wherein the divalent metallic cation is in the form of a salt.

5. The fluid composition in accordance with claim 1 wherein the fluorochrome is an antibiotic containing a chromomycinone complex.

6. The fluid composition in accordance with claim 1 wherein the fluorochrome is selected from the group consisting of aureolic acid, chromomycin, and olivomycin.

7. The fluid composition in accordance with claim 1 wherein the fluorochrome is mithramycin.

8. The fluid composition in accordance with claim 1 wherein the compatible surfactant is a salt of a higher alkyl sulfonate.

9. The fluid composition in accordance with claim 8 wherein the higher alkyl sulfonate is dodecyl sulfonate.

10. The fluid composition in accordance with claim 1 which further comprises a small concentration of a compatible penetrating agent.

11. The fluid composition in accordance with claim 10 wherein the penetrating agent is dimethyl sulfoxide.

12. A method for selectively detecting and determining the intracellular content of double stranded, helical DNA in the presence of cellular debris comprising:
   providing a sample cell culture;
   solubilizing the cell culture;
   admixing the solubilized cell culture with a fluid composition comprising a divalent metallic cation cofactor, and a fluorochrome which in the presence of the cofactor is capable of significant fluorescence enhancement upon interaction with double stranded, helical DNA; and
   determining the extent of fluorescence enhancement by comparing the fluorescence of the admixed solubilized cell culture and fluid composition relative to fluorescence of the fluid composition alone, said fluorescence enhancement being a measure of the intracellular content of double stranded helical DNA.

13. The method in accordance with claim 12 wherein the divalent metallic cation is $Mg^{+2}$, $Mn^{+2}$, $Zn^{+2}$ or $Co^{+2}$.

14. The method in accordance with claim 12 wherein the fluorochrome is an antibiotic containing a chromomycinone complex.

15. The method in accordance with claim 12 wherein the fluorochrome is an antibiotic compound selected from the group consisting of aureolic acid, chromomycin, and olivomycin.

16. The method in accordance with claim 12 wherein the fluorochrome is mithramycin.

17. The method in accordance with claim 12 wherein the fluid composition comprises $Mg^{+2}$ as the divalent metallic cation cofactor and mithramycin as the fluorochrome.

18. The method in accordance with claim 12 wherein the cell culture is solubilized by sonification.

19. The method in accordance with claim 12 wherein the fluid composition further includes a compatible surfactant, the surfactant effective to enhance solubilization of the cell culture.

20. The method in accordance with claim 19 wherein the higher alkyl sulfonate is dodecyl sulfonate.

21. The method in accordance with claim 12 wherein the fluid composition further includes a compatible penetrating agent.

22. The method in accordance with claim 21 wherein the penetrating agent is dimethyl sulfoxide.

23. A method for assessing lymphocyte activation, wherein the intracellular content of DNA is a measure of lymphocyte activation, the method comprising:
providing a lymphocyte cell culture sample;
stimulating the lymphocyte cell culture sample with a mitogen or antigen;
incubating the stimulated cell culture for a suitable period of time sufficient to induce intracellular synthesis of DNA;
solubilizing the mitogen stimulated lymphocyte cell culture after the incubation period;
admixing the solubilized cell culture with a fluid composition comprising a divalent metallic cation cofactor, and a fluorochrome which in the presence of the cofactor is capable of significant fluorescent enhancement upon interaction with double stranded helical DNA; and
determining the extent of fluorescence enhancement by comparing the fluorescence of the admixed solubilized cell culture and fluid composition relative to the fluorescence of the fluid composition alone, said fluorescence enhancement being a measure of intracellular double-stranded helical DNA.

24. The method in accordance with claim 23 wherein the divalent metallic cation is $Mg^{+2}$, $Mn^{+2}$, $Zn^{+2}$ or $Co^{+2}$.

25. The method in accordance with claim 23 wherein the fluorochrome is an antibiotic containing a chromomycinone complex.

26. The method in accordance with claim 23 wherein the fluorochrome is an antibiotic compound selected from the group consisting of aureolic acid, chromomycin, and olivomycin.

27. The method in accordance with claim 23 wherein the fluorochrome is mithramycin.

28. The method in accordance with claim 23 wherein the fluid composition comprises $Mg^{+2}$ as the divalent metallic cation cofactor and mithramycin as the fluorochrome.

29. The method in accordance with claim 29 wherein the cell culture is solubilized by sonification.

30. The method in accordance with claim 23 wherein the fluid composition further includes a compatible surfactant, the surfactant effective to enhance solubilization of the cell culture.

31. The method in accordance with claim 30 wherein the higher alkyl sulfonate is dodecyl sulfonate.

32. The method in accordance with claim 23 wherein the fluid composition further includes a compatible penetrating agent.

33. The method in accordance with claim 32 wherein the penetrating agent is dimethyl sulfoxide.

34. A method for the determination of the extent of binding to a double-stranded helical DNA of a test compound relative to displacement of DNA bound fluorochrome, the method comprising:
providing double stranded, helical DNA;
providing said test compound;
providing a composition comprising a divalent metallic cation cofactor, and the fluorochrome which in the presence of the cofactor is capable of fluorescence enhancement upon binding with double stranded helical DNA;
admixing said compound and composition together with double-stranded, helical DNA under conditions suitable for the binding of both the test compound and fluorochrome to double-stranded, helical DNA; and
determining the extent of binding of the test compound to double-stranded, helical DNA by comparing the difference of the fluorescence associated with the admixture containing the test compound, composition and DNA relative to the fluorescence associated with a combination of the composition and DNA.

35. The method in accordance with claim 34 wherein the divalent metallic cation is $Mg^{+2}$, $Mn^{+2}$, $Zn^{+2}$ or $Co^{+2}$.

36. The method in accordance with claim 34 wherein the fluorochrome is an antibiotic containing a chromomycinone complex.

37. The method in accordance with claim 34 wherein the fluorochrome is an antibiotic compound selected from the group consisting of aureolic acid, chromomycin, and olivomycin.

38. The method in accordance with claim 34 wherein the fluorochrome is mithramycin.

39. The method in accordance with claim 34 wherein the fluid composition comprises $Mg^{+2}$ as the divalent metallic cation cofactor and mithramycin as the fluorochrome.

40. The method in accordance with claim 34 wherein the composition is provided as an aqueous solution.

41. The method in accordance with claim 34 wherein the composition is provided as a dried dispersion on a solid-phase support material.

42. The method in accordance with claim 41 wherein the solid-phase support material is a cellulosic material.

* * * * *